(12) United States Patent
Marechal et al.

(10) Patent No.: US 11,436,722 B2
(45) Date of Patent: Sep. 6, 2022

(54) METHOD AND SYSTEM FOR FAST ASSESSMENT OF BRAIN CHANGE NORMALITY

(71) Applicant: SIEMENS HEALTHCARE GMBH, Erlangen (DE)

(72) Inventors: Benedicte Marechal, Lausanne (CH); Ricardo Alberto Corredor Jerez, Lausanne (CH); Jonas Richiardi, Geneva (CH)

(73) Assignee: Siemens Healthcare GmbH, Erlangen (DE)

( * ) Notice: Subject to any disclaimer, the term of this patent is extended or adjusted under 35 U.S.C. 154(b) by 219 days.

(21) Appl. No.: 16/820,910

(22) Filed: Mar. 17, 2020

(65) Prior Publication Data

US 2020/0302601 A1 Sep. 24, 2020

(30) Foreign Application Priority Data

Mar. 20, 2019 (EP) .................................... 19164053

(51) Int. Cl.
*G06T 7/00* (2017.01)
*G06T 7/62* (2017.01)
(Continued)

(52) U.S. Cl.
CPC ............ *G06T 7/0012* (2013.01); *A61B 5/055* (2013.01); *A61B 5/4064* (2013.01);
(Continued)

(58) Field of Classification Search
CPC ......... G06T 7/0012; G06T 7/11; G06T 7/194; G06T 7/251; G06T 7/62; G06T 2200/04;
(Continued)

(56) References Cited

U.S. PATENT DOCUMENTS 9,271,651 B2 * 3/2016 Avinash ................... A61B 5/00
9,390,509 B2 7/2016 Ono et al.
(Continued)

FOREIGN PATENT DOCUMENTS

EP 2762072 A1 8/2014

OTHER PUBLICATIONS

Lau J C et al: "Longitudinal neuroanatomical changes determined by deformation-based morphometry in a mouse model of Alzheimer's disease", Neuroimage, Elsevier, Amsterdam, NL, vol. 42, No. 1, 2008, pp. 19-27, XP023176255, ISSN: 1053-8119, DOI: 10.1016/J.NEUROIMAGE.2008.04.252, [retrieved on May 7, 2008].

*Primary Examiner* — Emily C Terrell
*Assistant Examiner* — Molly Wilburn
(74) *Attorney, Agent, or Firm* — Laurence A. Greenberg; Werner H. Stemer; Ralph E. Locher

(57) ABSTRACT

A system and a method measure volumetric changes of brain structures. The method includes initializing an intensity value of all voxels of a 3D voxel dataset representing the brain of a subject to an initial value preferentially equal to 0. For all voxels that belong to a segmented brain structure for which reference data of a longitudinal reference model exists, automatically executing the following steps: calculating a deviation of a volume change for the segmented brain structure from the longitudinal reference model, normalizing the deviation to obtain a quantitative value of the volume change on a same scale for voxel's belonging to different brain structures; and setting the intensity value of the voxels to the previously obtained quantitative value Q. The voxels of the 3D voxel dataset are displayed in a form of a longitudinal deviation map.

5 Claims, 3 Drawing Sheets

(51) Int. Cl.
*G06T 7/194* (2017.01)
*G06T 7/11* (2017.01)
*G06T 7/246* (2017.01)
*A61B 5/055* (2006.01)
*A61B 5/00* (2006.01)

(52) U.S. Cl.
CPC .............. *A61B 5/4088* (2013.01); *G06T 7/11* (2017.01); *G06T 7/194* (2017.01); *G06T 7/251* (2017.01); *G06T 7/62* (2017.01); *G06T 2200/04* (2013.01); *G06T 2207/10088* (2013.01); *G06T 2207/30016* (2013.01)

(58) Field of Classification Search
CPC . G06T 2207/10088; G06T 2207/30016; G06T 7/0016; A61B 5/055; A61B 5/4064; A61B 5/4088
See application file for complete search history.

(56) References Cited

U.S. PATENT DOCUMENTS

| | | | |
|---|---|---|---|
| 2011/0129129 A1* | 6/2011 | Avinash | A61B 5/4076 382/128 |
| 2011/0218405 A1* | 9/2011 | Avinash | G16H 40/63 600/300 |
| 2012/0051608 A1 | 3/2012 | Avinash et al. | |
| 2014/0341471 A1* | 11/2014 | Ono | A61B 5/0042 382/173 |
| 2015/0045651 A1* | 2/2015 | Crainiceanu | G01R 33/3614 600/410 |
| 2016/0012581 A1* | 1/2016 | Grandy | G06T 7/0012 382/128 |
| 2020/0029918 A1* | 1/2020 | Li | A61B 6/037 |

* cited by examiner

METHOD AND SYSTEM FOR FAST ASSESSMENT OF BRAIN CHANGE NORMALITY

CROSS-REFERENCE TO RELATED APPLICATION

This application claims the priority, under 35 U.S.C. § 119, of European application EP19164053, filed Mar. 20, 2019; the prior application is herewith incorporated by reference in its entirety.

BACKGROUND OF THE INVENTION

Field of the Invention

The present disclosure is directed, in general, to imaging techniques for imaging biological tissues, and more specifically to the use of magnetic resonance imaging (MRI) for measuring brain structures volume change.

The volumetric change of certain predefined tissue structures and tissue classes and its comparison with an age and gender related reference population adds important clinical information to the reading procedure of radiological data. An important example for these applications is given by clinical MR brain examinations to assess neurological disorders, such as Multiple Sclerosis, Alzheimer, MCI and dementia in general.

Usually, a dataset, e.g. a T1w MRI brain volume scan, is acquired and automatically segmented into a set of brain structures and tissue classes of interest. Simultaneously, previously acquired datasets (typically same T1w MRI scanning procedure) are automatically fetched and segmented into the same set of brain structures and tissue classes. For each segmented object of each time point, its volumetric value is calculated in absolute values. The annualized change of these volumetric values may be achieved by calculating the percentage of volume change per year compared to the previous scan. The annualized volume change values can then be compared to an age and gender dependent model of reference values for each brain structure hence providing clinicians with the mean to quantitatively assess the normality of brain structures volume change. There are various ways to create age and gender dependent models for this purpose—popular choices are linear regression or log-linear regression models.

For brain applications, the number of different brain structures of interest for a particular neurological disease and related structural changes is typically large. For instance, the number of brain structures of interest can easily exceed ten and in a typical scenario, some 40 brain structures may be treated and modeled individually. In general, corresponding quantitative values as well as reference values are summarized in a table which represents a significant amount of information to be interpreted.

For instance, clinicians use tabular reports of all annualized percent change values for each structure that is segmented and modeled, wherein values falling out of the reference range are usually flagged. Also trending plot of regression model of the reference data together with given patient's normalized values might be used for pointing out volume changes. The analysis of the tabular reports might also be time consuming depending on the case.

In addition, such applications not only require assessing deviations from the model of reference values, but also to know whether the volume change deviations are abnormally atrophic or hypertrophic, e.g. in neuro degeneration or inflammatory diseases assessment, an abnormally atrophic deviation from the reference population is considered relevant for all grey matter and white matter based brain structures whereas an abnormally hypertrophic deviation from the reference population is relevant for all cerebrospinal fluid (CSF) filled structures. It remains thus important to develop a tool that would help clinicians to quickly get precise information regarding volumetric change of brain structures.

BRIEF SUMMARY OF THE INVENTION

An objective of the present invention is to propose a method and a system for automatically determining volumetric changes of predefined tissue structures and tissue classes of a brain, which is not biased towards a specific pattern of a disease, which is capable of providing results for multiple structures of the brain at the same time, which is providing preferentially all volumetric changes of the whole brain, in a concise, precise, and fast way compared to existing techniques.

With the foregoing and other objects in view there is provided, in accordance with the invention, a method for measuring volumetric changes of brain structures. The method includes i) initializing an intensity value of all voxels of a 3D voxel dataset representing a brain of a subject to an initial value preferentially equal to 0; and ii) automatically executing the now described sub-steps for all the voxels that belong to a segmented brain structure for which reference data of a longitudinal reference model exists. A deviation of a volume change for the segmented brain structure is calculated from the longitudinal reference model. The deviation is normalized to obtain a quantitative value of the volume change in order to compare the deviation for the voxels belonging to different brain structures and the intensity value of the voxels of the segmented brain structure is set to the quantitative value previously obtained. The voxels of the 3D voxel dataset are displayed in a longitudinal deviation map.

The objective is achieved according to the present invention by a method and a system for measuring volumetric changes of brain structures according to the object of the independent claims. Dependent claims present further advantages of the invention.

According to the present invention, a method for measuring volumetric changes of brain structures contains an automatic determination of a longitudinal deviation map for an individual patient. The longitudinal deviation map contains a dense 3D voxel dataset of the patient brain, and individual voxel's value of the dataset represents the brain structure's volume change deviation from a longitudinal reference model that is a model of the brain structure to which the voxel belongs to. A system configured for carrying out the claimed method is also proposed. For each brain structure of interest, longitudinal data are therefore collected for the individual patient and compared to a longitudinal reference model obtained for the brain structure. The longitudinal reference model is typically obtained from collecting the longitudinal data for each brain structure of interest for a group of healthy persons serving as reference population.

The foregoing has outlined rather broadly the features and technical advantages of the present disclosure so that those skilled in the art may better understand the detailed description that follows. In particular, the present invention may help a physician to monitor volumetric changes of brain structures during health control of a subject.

Additional features and advantages of the disclosure will be described hereinafter that form the object of the claims. Those skilled in the art will appreciate that they may readily use the concept and the specific embodiment disclosed as a basis for modifying or designing other structures for carrying out the same purposes of the present disclosure. Those skilled in the art will also realize that such equivalent constructions do not depart from the spirit and scope of the disclosure in its broadest form.

For a more complete understanding of the present disclosure, and the advantages thereof, reference is now made to the following descriptions taken in conjunction with the accompanying drawings, wherein like numbers designate like objects.

Other features which are considered as characteristic for the invention are set forth in the appended claims.

Although the invention is illustrated and described herein as embodied in a method and a system for fast assessment of brain change normality, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
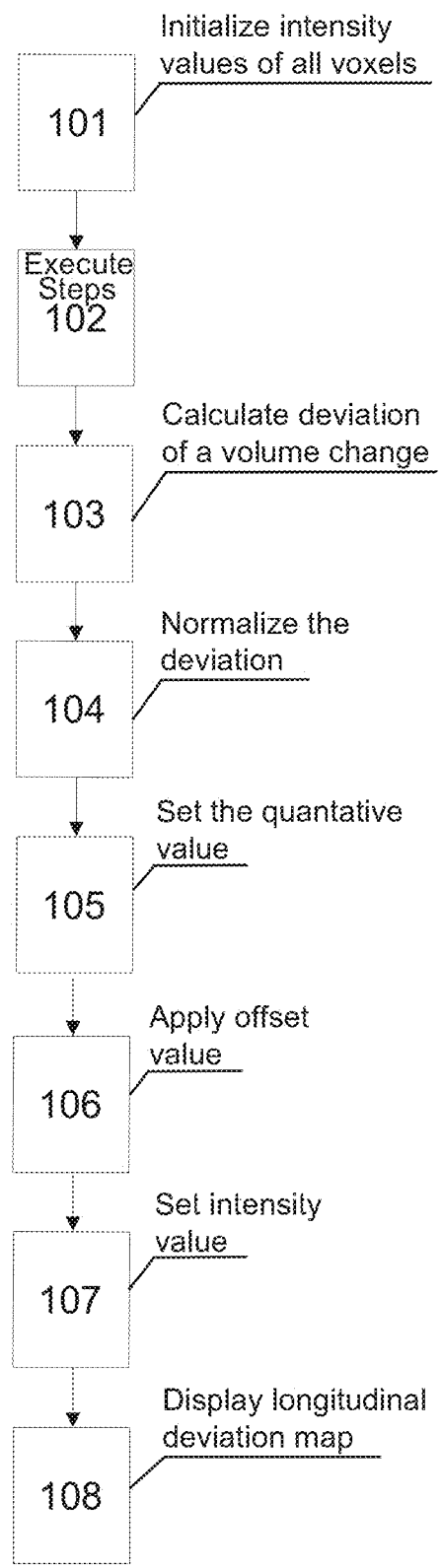
FIG. 1 is a flowchart illustrating a method for measuring volumetric changes of brain structures according to the invention.
Figure 2:
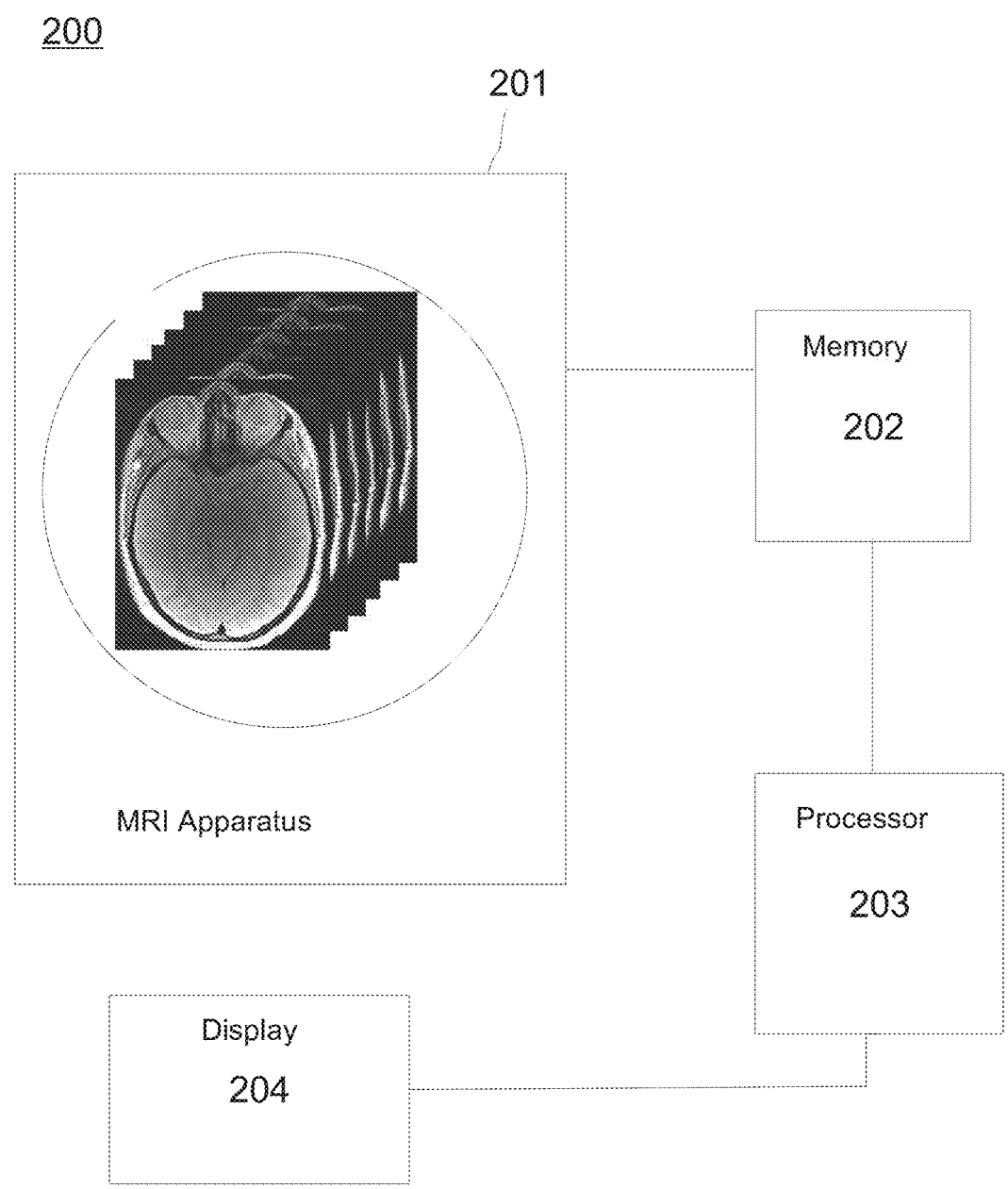
FIG. 2 is a block diagram illustrating a system for implementing the method.
Figure 3:
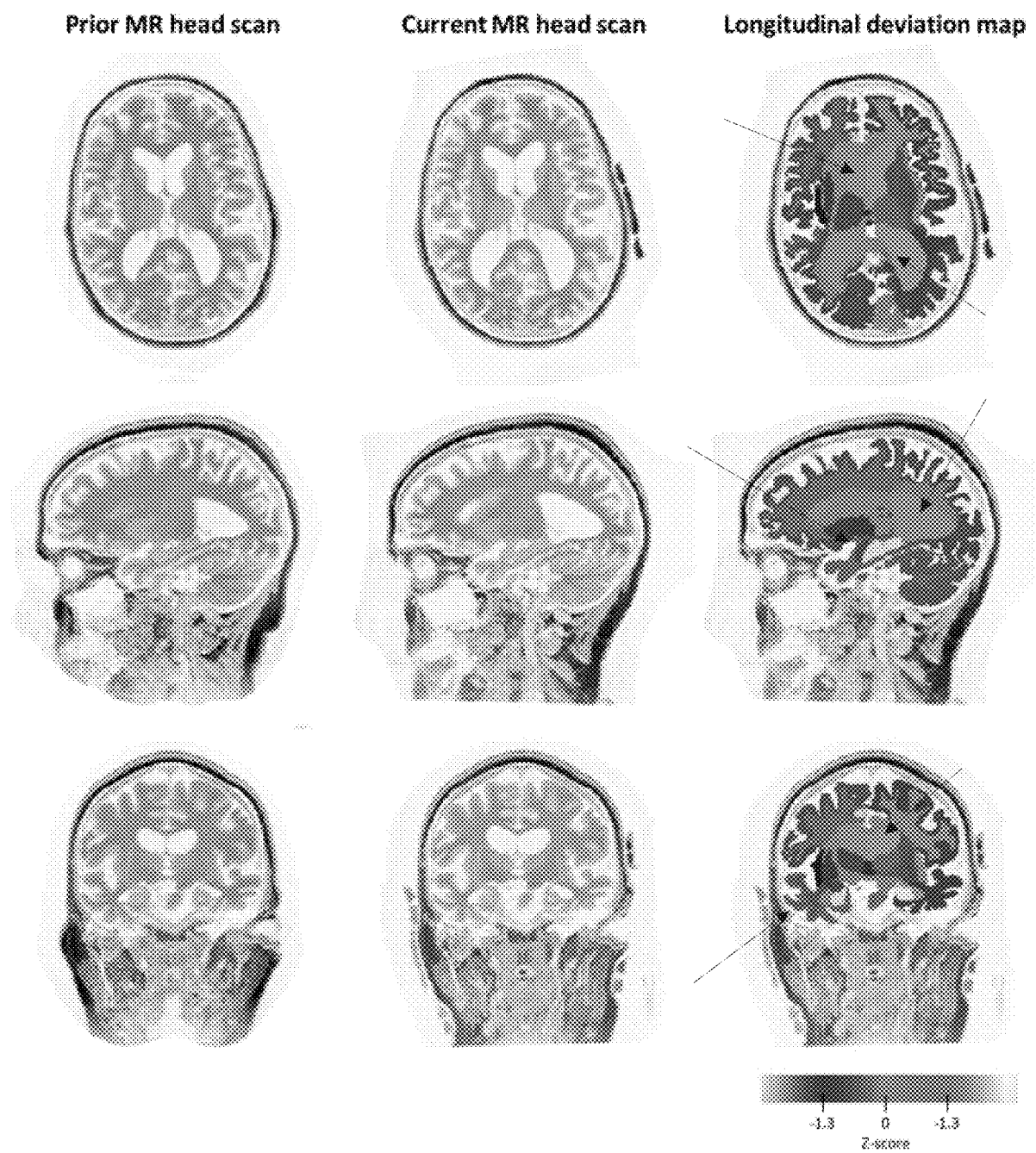
FIG. 3 shows illustrations of longitudinal deviation maps obtained according to the invention.

Referring now to the figures of the drawings in detail and first, particularly to FIGS. 1-3 thereof, there are shown various embodiments used to describe the principles of the instant disclosure in this patent application and are by way of illustration only and should not be construed in any way to limit the scope of the disclosure. Those skilled in the art will understand that the principles of the present disclosure may be implemented in any suitably arranged device. The numerous innovative teachings of the present application will be described with reference to exemplary non-limiting embodiments.

FIG. 1 describes the different steps of the method 100 for measuring volumetric changes of brain structures according to the invention. The method 100 proposes in particular to measure the volumetric changes by calculating, and then displaying, a longitudinal deviation map for an individual patient according to the following steps:

i) at step 101, the system initializes an intensity value of all voxels of a 3D voxel dataset representing the brain of an individual patient to an initial value preferentially equal to 0;

ii) at step 102, and for all voxels that belong to a segmented brain structure for which reference data of a longitudinal reference model exists, the system automatically executes the following steps:

iia) at step 103, it calculates, for the segmented brain structure, a deviation D of a volume change in function of time, e.g. annualized, from the longitudinal reference model, wherein for each segmented brain structure, there is a longitudinal reference model representing the volume change of the structure in function of time for a healthy population. In particular, the same time scale for the volume change in function of time is used for the model and for the patient when calculating the deviation D. Usually, the time scale unit for representing the volume change in function of time is the month or the year when calculating the deviation D. The volume change for the patient is typically obtained by measuring the volume of the brain structure at different times and automatically determining the change of said volume in function of time, e.g. the annualized or monthly change of volume;

iib) at step 104, it normalizes the deviation D to obtain a quantitative value Q of the volume change enabling a comparison of the deviation D for voxel's belonging to different brain structures, said quantitative value Q being for instance represented on a same scale for all brain voxels. Depending on the longitudinal reference model, different techniques might be used for normalizing the deviation D. For instance, if the longitudinal reference model is a linear Gaussian regression model, the normalized deviation D could be given in terms of the standard deviation (Z-Scores) for the respective brain structure. If the longitudinal reference model is a percentile model, the normalized deviation D could then be given in terms of percentiles;

iic) at step 105 and optionally, if only pathologic deviations D have to be determined, then the system automatically sets the quantitative value Q of the normalized deviation D equal to 0 if the deviation D represents, preferentially within a predefined timeframe, an atrophy for CSF or ventricle brain structures or if the deviation D represents, preferentially within the predefined timeframe, a hypertrophy for GM/WM brain structures, otherwise the quantitative value Q of the normalized deviation D remains unchanged. The timeframe is for instance comprised between 1 and 5 years, preferentially more than 2 years;

iid) at step 106 and optionally, the system automatically applies an offset value O to the quantitative value Q of the normalized deviation D in order to obtain a new quantitative value Q'=Q+O, wherein the offset value O is configured for enabling a separation or differentiation between a background containing all voxels with value equal to the initial value from a foreground containing all voxels whose value is different from the initial value. Advantageously, the offset value O makes a visual separation between voxels that are part of the assessed brain structures and others which were either not part of the segmentation or for which there is no reference information available possible. In other words, an offset value is added to the deviation quantitative value if the respective anatomical area was not segmented or if no information relating to the respective anatomical area exists in the reference model (i.e., there is no normative range for such area);

iie) at step 107, the system sets the intensity value of the voxels (i.e. of all voxels of the segmented brain structure) to the previously obtained quantitative value Q (if step 106 did not take place) or Q' (if step 106 took place);

iif) at step 108, notably after repeating step ii, for each segmented brain structure for which the longitudinal reference model exists, the system displays the voxels of the 3D voxel dataset in a longitudinal deviation map. Wherein optionally a color mapping is applied to the voxel intensity values to characterize the deviation of the volume change of all voxels belonging to the segmented brain structure from the volume change provided by the longitudinal reference model for the segmented brain structure, e.g., red to blue gradient. Advantageously, the color mapping enables a user to quickly appreciate a distance to reference range (i.e. a difference between the volume change of the patient and the volume change measured for the healthy population), the distance to reference range showing for instance the degree of abnormal atrophy/hypertrophy.

Displaying the voxels results thus in a 3D image which allows a very fast visual and quantitative assessment of the volumetric change of a patient in comparison to a reference population on which the longitudinal reference model is based. Preferentially, the computation of the longitudinal reference model is performed off-line, and only once, providing therefore fixed data.

FIG. 2 illustrates a system 200 for measuring volumetric changes of brain structures of a subject. The system contains optionally, a magnetic resonance imaging (MRI) apparatus 201 configured for acquiring brain structural images for a subject and extracting for the subject volumetric information for a set of predefined brain regions. A database 202 or memory is provided for storing longitudinal data with respect to the volumetric information of each set of predefined brain regions for a healthy population, i.e. a group of healthy persons, so as to create and store a longitudinal reference model from volumetric information data collected by the MRI apparatus 201 or another suitable system.

A processing unit 203 is provided for calculating a deviation of brain structure's volume of an individual patient with respect to a reference brain structure volume obtained from the longitudinal reference model. A display 204 is provided for displaying a longitudinal deviation map, wherein the intensity value of each voxel represents a volumetric deviation with respect to a reference value obtained for the voxel from the longitudinal reference model.

The system 200 according to the invention is configured for performing the steps of the method for calculating and then displaying the deviation.

Finally, FIG. 3 shows typical longitudinal deviation maps as obtained when carrying out the claimed method with the system according to the invention. Volumetric deviations (see arrows) might be quickly identified by a physician, notably due to a color mapping.

The present invention provides therefore the following advantages with respect to current techniques:

a) it automatically provides physicians with both visualization and quantification of brain atrophy normality in multiple structures of the brain at the same time, thus enabling them to reach a faster, more detailed and accurate analysis;

b) it is not biased towards finding a particular pattern of disease, unless specific pathologic deviations are encoded according to step 105;

c) it is computationally very cheap;

d) it is a new way to visualize the longitudinal deviation from a reference population on a coarse segmentation object-based level;

e) it allows encoding longitudinal deviations from a reference population database which provides physicians with additional information compared to values summarized in a table;

f) the longitudinal deviation maps provide a direct visualization of volume changes with respect to location within the brain, which was not possible with respect to prior art technique in the form of the tabular report of brain volume change data;

g) the longitudinal deviation maps are quantitative with respect to the underlying model: they offer a visual way to compare multiple time points. Thus, abnormally atrophic/hypertrophic patterns of certain structures over time can easily be spotted.

Those skilled in the art will recognize that many other statistical models could be used to estimate deviation values (annual percent change), including parametric models with different assumptions about regression residuals, semi-parametric models, non-parametric models, or Bayesian techniques with various specifications for prior distributions, each having drawbacks and advantages known to those skilled in the art. Also, the visualization of the deviations itself might be achieved according to different techniques known in the art, going from purely abstract techniques (such as a chart with the anatomical structure name, ranging from parallel plot to radar plot as in ICOMETRIX cross-sectional solution) to color-coded 3D surface mesh with various cutout planes.

The invention claimed is:

1. A method for measuring volumetric changes of brain structures, which comprises the steps of:
   i) initializing an intensity value of all voxels of a 3D voxel dataset representing a brain of a subject to an initial value preferentially equal to 0;
   ii) automatically executing the following sub-steps for all the voxels that belong to a segmented brain structure for which reference data of a longitudinal reference model exists:
      iia) calculating a deviation of a volume change for the segmented brain structure from the longitudinal reference model;
      iib) normalizing the deviation to obtain a quantitative value Q of the volume change in order to compare the deviation for the voxels belonging to different brain structures;
      iic) setting the intensity value of the voxels of the segmented brain structure to the quantitative value Q previously obtained; and
   iii) displaying the voxels of the 3D voxel dataset in a longitudinal deviation map.

2. The method according to claim 1, wherein if only pathologic deviations have to be determined, then a system automatically sets the quantitative value Q of a normalized deviation equal to 0 if the deviation represents an atrophy for cerebrospinal fluid (CSF) or ventricle brain structures or if the deviation represents a hypertrophy for grey matter/white matter (GM/WM) brain structures, otherwise the quantitative value Q of the normalized deviation remains unchanged.

3. The method according to claim 1, which further comprises automatically applying an offset value O to the quantitative value Q of the normalized deviation in order to obtain a new quantitative value Q'=Q+O, wherein the offset value O is configured for enabling a separation or differentiation between a background containing all the voxels with value equal to the initial value from a foreground containing all the voxels whose value is different from the initial value, and wherein the intensity value of the voxel is then automatically set to the new quantitative value Q' instead of the quantitative value Q in the setting step.

4. The method according to claim 1, which further comprises applying a color mapping to voxel intensity values to characterize the deviation of the volume change of each of the voxels from a volume of the longitudinal reference model.

5. A system for measuring volumetric changes of brain structures of a subject, the system comprising:
   optionally, a magnetic resonance imaging (MRI) apparatus configured for acquiring brain structural images for the subject and extracting for the subject volumetric information for a set of predefined brain regions;
   a database for storing longitudinal data with respect to the volumetric information of each of the predefined brain regions for a group of healthy subjects so as to create and store a longitudinal reference model from the volumetric information data collected by said MRI apparatus or another suitable system;
   a processor for calculating a deviation of a brain structure's volume deviation of a new subject with respect to a reference brain structure volume obtained from the longitudinal reference model;
   a display for displaying a longitudinal deviation map, wherein an intensity value of each voxel represents a volumetric deviation with respect to a reference value obtained for the voxel from the longitudinal reference model for the new subject;
   the system configured for performing steps of a method for calculating and then displaying the longitudinal deviation map, the system configured to measure the volumetric changes of the brain structures, which comprises the steps of:
   i) initializing the intensity value of all voxels of a 3D voxel dataset representing a brain of the subject to an initial value preferentially equal to 0;
   ii) automatically executing the following sub-steps for all the voxels that belong to a segmented brain structure for which reference data of the longitudinal reference model exists:
      iia) calculating a deviation of a volume change for the segmented brain structure from the longitudinal reference model;
      iib) normalizing the deviation to obtain a quantitative value Q of the volume change in order to compare the deviation for the voxels belonging to different brain structures;
      iic) setting the intensity value of the voxels of the segmented brain structure to the quantitative value Q previously obtained; and
   iii) displaying the voxels of the 3D voxel dataset in the longitudinal deviation map.

* * * * *